United States Patent
Lewis

(10) Patent No.: US 8,308,689 B2
(45) Date of Patent: Nov. 13, 2012

(54) DRIVE RAM FOR MEDICAL INJECTORS

(75) Inventor: Frank M. Lewis, Fairfield, OH (US)

(73) Assignee: Mallinckrodt LLC, Hazelwood, MO (US)

(*) Notice: Subject to any disclaimer, the term of this patent is extended or adjusted under 35 U.S.C. 154(b) by 95 days.

(21) Appl. No.: 12/665,739

(22) PCT Filed: Aug. 5, 2008

(86) PCT No.: PCT/US2008/072176
§ 371 (c)(1),
(2), (4) Date: Dec. 21, 2009

(87) PCT Pub. No.: WO2009/023463
PCT Pub. Date: Feb. 19, 2009

(65) Prior Publication Data
US 2011/0009826 A1    Jan. 13, 2011

Related U.S. Application Data

(60) Provisional application No. 60/955,496, filed on Aug. 13, 2007.

(51) Int. Cl.
*A61M 5/142* (2006.01)
(52) U.S. Cl. ........ 604/154; 604/151; 604/155; 604/156; 604/240
(58) Field of Classification Search .......... 604/150–151, 604/154–156, 187, 218, 228, 232–233, 240; 128/DIG. 1
See application file for complete search history.

(56) References Cited

U.S. PATENT DOCUMENTS

| | | | |
|---|---|---|---|
| 4,234,223 A | 11/1980 | O'Neil | |
| 4,677,960 A | 7/1987 | Ward | |
| 4,677,980 A | 7/1987 | Reilly et al. | |
| 4,695,271 A | 9/1987 | Goethel | |
| 4,775,363 A | 10/1988 | Sandsdalen | |
| 5,279,569 A | 1/1994 | Neer et al. | |
| 5,300,031 A | 4/1994 | Neer et al. | |
| 5,451,211 A | 9/1995 | Neer et al. | |
| 5,456,669 A | 10/1995 | Neer et al. | |
| 5,658,261 A * | 8/1997 | Neer et al. | 604/240 |
| 5,662,612 A | 9/1997 | Niehoff | |
| 5,693,113 A | 12/1997 | Dries et al. | |
| 5,868,710 A | 2/1999 | Battiato et al. | |
| 5,921,967 A | 7/1999 | Sadowski et al. | |
| 6,315,758 B1 | 11/2001 | Neer et al. | |
| 6,432,089 B1 | 8/2002 | Kakimi et al. | |
| 6,533,758 B1 | 3/2003 | Saats et al. | |
| 6,585,700 B1 | 7/2003 | Trocki et al. | |
| 6,659,979 B2 | 12/2003 | Neer et al. | |
| 6,764,466 B1 | 7/2004 | Saats et al. | |
| 2002/0022807 A1* | 2/2002 | Duchon et al. | 604/228 |
| 2005/0015056 A1 | 1/2005 | Duchon et al. | |
| 2006/0106347 A1 | 5/2006 | Fago et al. | |

* cited by examiner

*Primary Examiner* — Quynh-Nhu H Vu

(57) ABSTRACT

A drive ram (26) for use with a medical fluid injector may include a central, longitudinal reference axis (24). First and second gripper members (92) may be pivotally interconnected with a plunger engaging end (266) of the drive ram. Each of the first and second gripper members may be pivotable about a common pivot axis (95) that intersects the reference axis. Each of the gripper members may further include a first end (102) that is remote from the common pivot axis. In some embodiments, the first and second gripper members may be pivotable between a first position and a second position. In the first position, the first ends of the gripper members may be spaced apart by a first distance, while in the second position, they may be spaced apart by a second distance that is greater than the first distance.

12 Claims, 4 Drawing Sheets

DRIVE RAM FOR MEDICAL INJECTORS

RELATED APPLICATIONS

This application is a U.S. National Stage of PCT/US08/72176, filed 5 Aug. 2008, which claims priority to U.S. provisional application Ser. No. 60/955,496 filed on 13 Aug. 2007 and entitled DRIVE RAM FOR MEDICAL INJECTORS. Priority is claimed to each patent application set forth in this Related Applications section.

TECHNICAL FIELD

This invention generally relates to medical fluid injectors, and more particularly to drive rams for use in such medical fluid injectors.

BACKGROUND

Medical fluid injectors are motorized devices that expel fluid, such as contrast media, from a syringe, through tubing, and into a subject such as a person or animal. Medical fluid injectors are generally adjustably fixed to a stand or support and have a drive ram that interfaces with a plunger of the syringe. This drive ram may be used to drive the plunger forward to expel fluid from the syringe and to pull the plunger rearward to draw fluid into the syringe.

Conventional injectors have included a variety of designs for engagement mechanisms that provide at least a temporary interface between the drive ram of the injector and the plunger of an associated syringe. However, there have been difficulties with such engagement mechanisms. For instance, some may say the engagement mechanism of one conventional injector may cause uneven loading of the plunger, which may contribute to leakage of fluid being drawn into and/or expelled out of the syringe. As another example, some may say the engagement mechanism of another conventional injector may tend to fail under the tensile load of a normal injection procedure, thus resulting in the drive ram slipping off of the plunger.

SUMMARY

The present invention, in at least some embodiments, is directed to the interface between the drive ram of an injector and the plunger of a syringe. In particular, certain embodiments of the invention are directed to what may be characterized as syringe grippers that are associated with the drive ram. Embodiments of these syringe grippers provide engagement between the drive ram of an injector and the plunger of a syringe that promotes effective filling and discharge of the syringe.

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In accordance with a first aspect of the invention, a drive ram for use with a medical fluid injector includes a central, longitudinal reference axis. A first gripper member is pivotally interconnected with a plunger engaging end of the drive ram. A second gripper member is also pivotally interconnected with the plunger engaging end of the drive ram. Each of the first and second gripper members is pivotable about a common pivot axis that intersects the reference axis. Each of the gripper members further includes a first end that is remote from the common pivot axis. In some embodiments, the first and second gripper members are pivotable between a first position and a second position. In the first position, the first ends of the gripper members are spaced apart by a first distance, while in the second position, they are spaced apart by a second distance that is greater than the first distance.

In specific embodiments of this first aspect, a biasing member such as a sphere or ball may be in contact with at least one of the gripper members and urge the gripper members toward the first position. The drive ram may have a pivot pin such that the common pivot axis extends centrally through a length of the pin. The gripper members may each include a second end that is opposite the first end and include an aperture such that at least a portion of the pivot pin is located within each of the apertures of the gripper members. In some embodiments, the gripper members may be configured to move in substantial unison between the first and second positions. In some embodiments, each of the gripper members may include a contact portion that is disposed about the common pivot axis and that exhibits a first thickness that is greater than a second thickness adjacent the contact portion. In some embodiments, the contact portions of the gripper members may be in contact with one another.

Each of the gripper members may include a finger which extends from the contact portion in a direction toward the other gripper member. The gripper members may include respective ledges configured such that the finger on one gripper member engages the ledge of the other gripper member when the gripper members are in the first position. Each gripper member may have a main body portion and an arm, with the arm extending from the first end in a direction toward the longitudinal axis, so that the gripper members define a cavity therebetween.

A second aspect of the invention is directed to a drive ram for a medical fluid injector. This drive ram includes a pivot pin that is aligned with a longitudinal axis of the drive ram, and a gripper member that pivotally coupled to the pivot pin. This gripper member includes a gripper body having a first end and a second end. In addition, an aperture is defined in the second end of the gripper body to receive the pivot pin therethrough. The gripper member also includes an arm that extends outwardly from the first end of the gripper body and that is adapted to contact a corresponding engagement structure of a syringe plunger. This arm of the gripper member is spaced laterally from the longitudinal axis of the drive ram such that forces acting on the gripper member during movement of the drive ram to retract the plunger urge the gripper member in a direction toward the engagement structure of the plunger.

A third aspect of the invention is directed to a medical fluid injector that includes a drive ram described herein.

Still a fourth aspect of the invention is directed to a method of using a medical fluid injector. In this method, a syringe having a longitudinal reference axis is inserted into an aperture defined in the injector. While the syringe is located within the aperture in the injector, at least a portion of a plunger of the syringe is positioned between first and second members of the injector such that at least one of the members is in contact with at least a portion of the plunger. This positioning of the plunger generally includes pivoting the first and second members about a common pivot axis.

With regard to the fourth aspect of the invention, the first and second gripper members of the injector may be spaced apart by a first distance, where the gripper members are pivotally mounted on a common pivot pin. A feature of the plunger may be inserted between the gripper members, and the gripper members may be spaced apart to a second distance that is smaller than the first distance. In some embodiments, at least one of the gripper members may be urged (e.g., biased) toward the second distance.

Yet a fifth aspect of the invention is directed to a method of using a medical fluid injector. In this method, a syringe plunger is gripped by first and second gripper members of the injector. Further, a force is applied on the gripper members at a pivot point pivotally connecting the gripper members, such that the force urges the gripper members toward one another at points of engagement with the syringe plunger. In some embodiments, the force may be applied along a first axis generally aligned with a longitudinal axis of the plunger. The syringe plunger is then moved within and relative to a barrel of the syringe in a manner such that the syringe plunger moves away from a nozzle of the syringe.

In accordance with one or more aspects of the invention, a pair of gripper members pivotally mounted on a common pivot aligned with a central axis of the drive ram allows an injector to engage an engaging feature of a syringe plunger in a more secure manner than may be possible with conventional injectors. A gripper assembly of the invention may even facilitate secure engagement of what may be characterized as cocked or misaligned plungers. By securely engaging cocked or misaligned plungers, the likelihood of media leakage may be reduced. Because contact between gripper members of some gripper assemblies of the invention may be limited to respective contact portions, the likelihood of sticking (e.g., the gripper members being stuck together and not capable of movement relative to each other) may be reduced.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which.

DETAILED DESCRIPTION OF EXEMPLARY EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
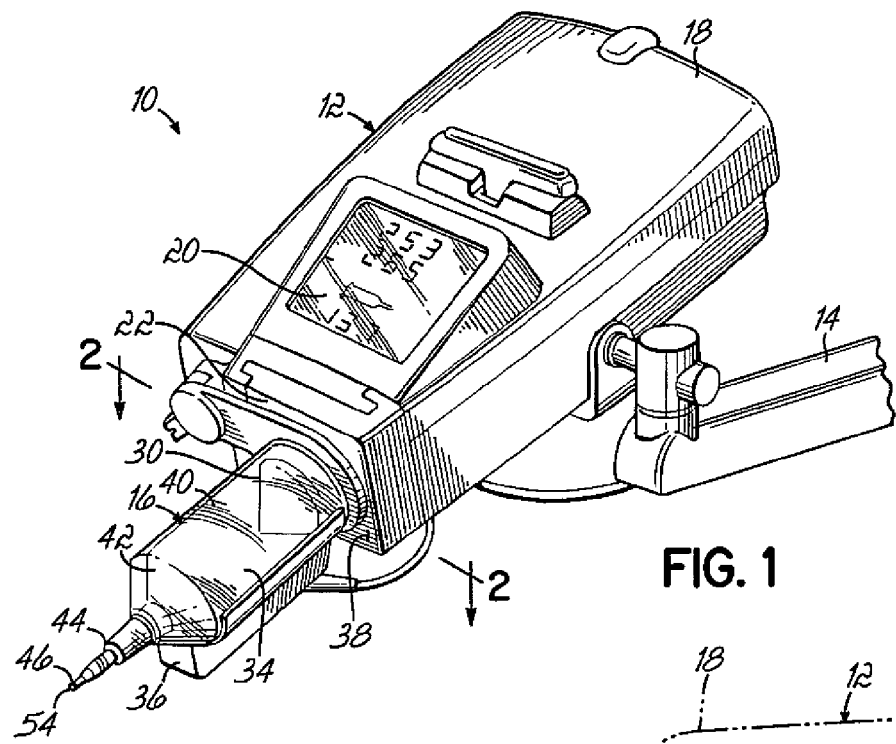
FIG. 1 is a perspective view of a medical fluid injector in accordance with principles of the present invention.
Figure 2A:
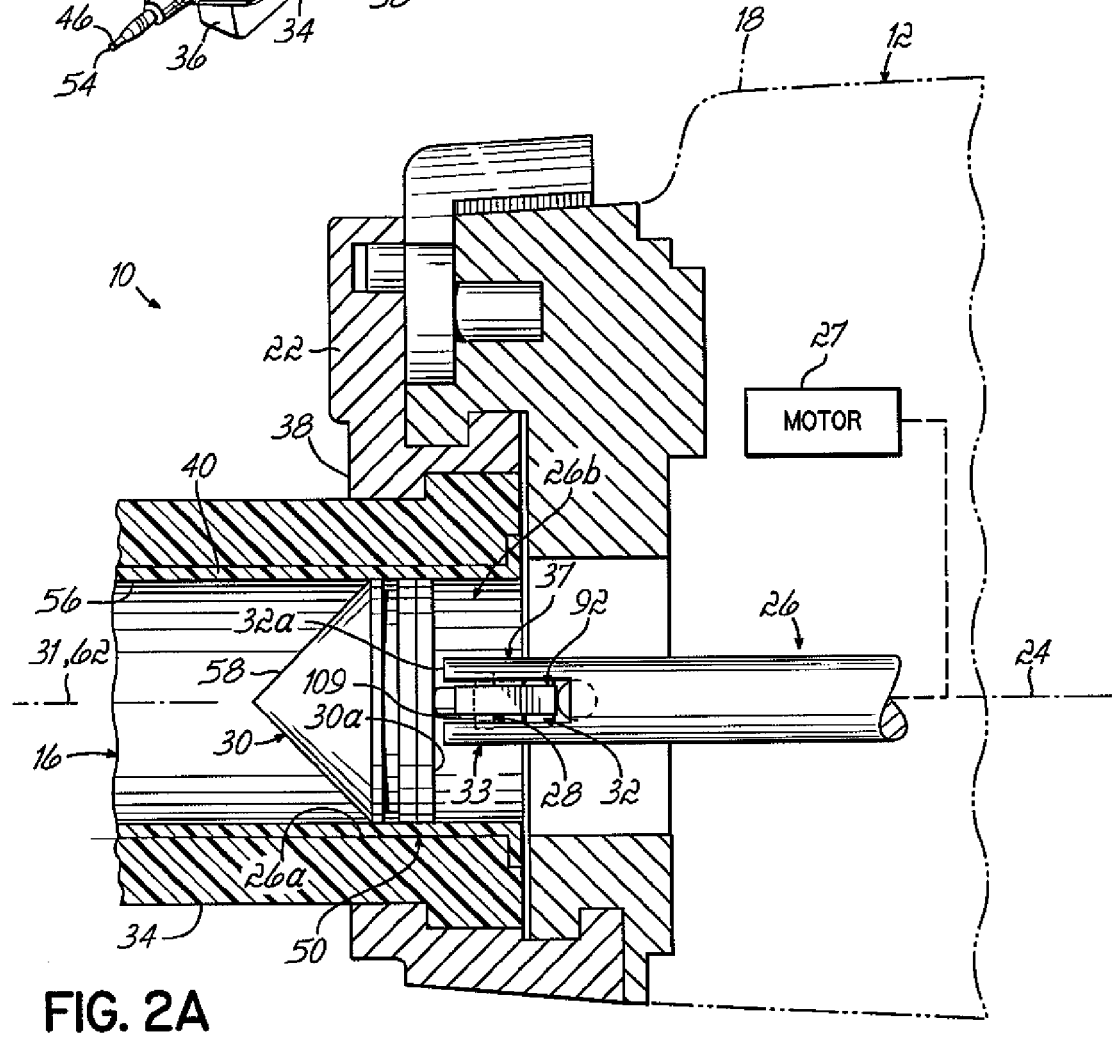
FIGS. 2A and 2B are partial cross-sectional views of the injector of FIG. 1 taken along line 2-2 of FIG. 1.
Figure 2B:
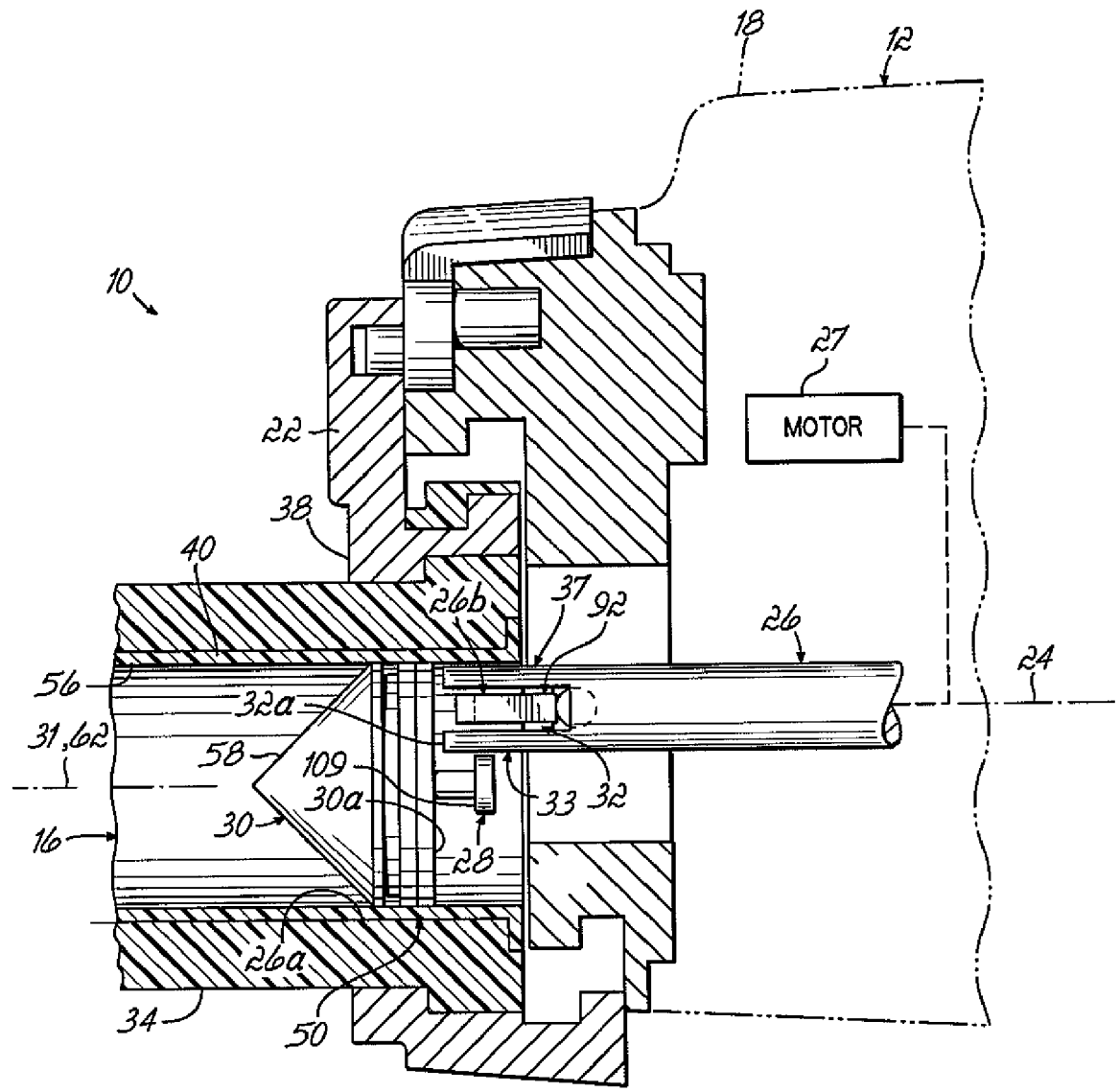

FIGS. 1, 2A and 2B show a medical fluid injector 10 that includes a power head 12 attached to an arm 14, which in turn may be mounted, for example, to a ceiling, wall, or on a carriage (not shown). This allows for motion of the power head 12 so that it may be positioned to receive and load a syringe 16, which has a longitudinal reference axis 16a, to inject fluids into, or aspirate fluids from, a subject (not shown). An injector of the type shown in FIGS. 1 and 2 is illustrated in further detail in U.S. Pat. No. 5,868,710. For example, and without limitation, fluids may be injected into a subject following one or more pre-programmed protocols, such as described in U.S. Pat. No. 5,662,612. Surrounding an inner mechanism of the injector 10 is an injector housing 18. The housing 18 includes a display panel 20 that aids an operator of the injector 10 (e.g., in monitoring amounts of fluid injected into or withdrawn from a subject). The housing 18 further includes an aperture 26a at that receives at least a portion of the syringe 16 therein.

Toward a forward end of the injector housing 18 is a face plate 22. The face plate 22 facilitates connection between the injector housing 18 and the syringe 16 and, in certain embodiments, facilitates disengagement of a feature such as a coupling element in the form of a button 28 of a syringe plunger 30 from a coupling mechanism or gripper assembly 32 disposed at or proximate a plunger engaging end 26b of the drive ram 26.

In an exemplary use, a syringe 16 may be loaded into and coupled to the injector 10, or a face plate thereof, thus placing the plunger and ram in a coaxial relationship with a drive ram 26 of the injector 10. In the embodiment shown in FIGS. 2A and 2B, the drive ram 26 extends to and from the housing 18 via an aperture 26a. In the embodiment shown in FIG. 2A, when in use the syringe 16 is generally coaxial with drive ram 26, that is, the longitudinal axis 24 of the drive ram 26 is substantially coaxial with the axis 31.

In the illustrated embodiment, face plate 22 is slidable along a plane perpendicular to the longitudinal reference axis 24 of drive ram 26. Two alternate positions of the face plate 22, respectively engaged and disengaged with the front surface of the injector housing, are shown in FIGS. 2A and 2B, respectively. The syringe axis 32 and plunger axis 62 is coaxial with the drive ram 26 when the face plate 26 is engaged to the injector front surface as shown in FIG. 2A, and the syringe is off axis of the drive ram 26 when the face plate 26 is disengaged with the injector front surface as shown in FIG. 2B. Transverse motion of the face plate 22 between the positions in FIG. 2A and FIG. 2B also engages and disengages the rearward extending button 28 of the syringe plunger 30 and the gripper assembly 32 of the plunger drive ram 26. As seen in FIG. 2A the button 28 is engaged with the gripper assembly 32 and as seen in FIG. 2B the button 28 is disengaged with the gripper assembly 32.

In certain embodiments, such as that shown in FIGS. 2A and 2B, the engagement and disengagement of the syringe may be effected at least in part by moving the face plate 22 to which the syringe is mounted, transverse to the longitudinal axis 24 of the plunger drive ram 26 between an engaged position such as shown in FIG. 2A and a disengaged position such as shown in FIG. 2B. In addition, or as an alternative to transverse motion, face plate 22 may be capable of pivotal motion between engaged and disengaged positions, as is seen in U.S. Pat. No. 5,658,261. Alternately, the drive ram may be capable of motion transverse to its axis 24 to engageable and disengaged positions, or a mechanism may be provided for causing disengagement of the gripper assembly without transverse motion of either.

It will be appreciated that face plate 22 or the injector (if no face plate is used) may permit front loading of a syringe onto the injector as illustrated in U.S. Pat. No. 5,658,261, or alternatively face plate 22 may permit rear loading of the syringe into the injector, within the contemplated scope of the present invention. In the case of rear loading, the face plate may be moved or tilted away from the front face of the injector, permitting a new syringe to be installed from the rear into the face plate 22 of the injector and/or to enable unloading and removal of a syringe from the face plate 22. Face plate disengagement of this type is known in the art such as in U.S. Pat. No. 4,695,271. Other forms of rear-loading are also known and within the scope of the present invention, such as rear loading through the use of a turreted face plate as shown in U.S. Pat. No. 4,677,980.

With continued reference to the specific embodiment of FIGS. 1-2, a pressure jacket 34, which may be transparent, extends outwardly from the face plate 22 and houses the syringe 16. The syringe 16 and pressure jacket 34 are constructed such that they collectively withstand injection pressures created by the injector 10 during an injection operation. It should be noted that some injectors, whether rear-, front- or side-loading, may not include a face plate (e.g., 22) and/or a pressure jacket (e.g., 34). For instance, a pressure jacket may not be required in lower pressure injection applications, or with the use of pressure resistant syringe materials such as polycarbonate.

A cradle 36 is operatively connected to the injector housing 18. In the illustrated embodiment, the cradle 36 extends from the front surface 38 of the face plate 22, and supports the syringe 16 and pressure jacket 34. The cradle 36 may include a mechanism to warm the contents of the syringe 16, thus allowing the contents of a syringe 16 to be maintained at a desired temperature while the syringe 16 is attached to the injector housing 18. The syringe 16 may then be held in proximity with the cradle 36 such that the medical fluid (e.g., contrast media, saline, etc.) within the syringe 16 may be warmed.

With continued reference to FIGS. 1-2, the syringe 16 includes an exterior cylindrical body 40, which, at its forward end, is integral with a conical front wall 42. A neck 44, terminating in discharge tip 46, extends forwardly from and is integral with the front wall 42. The body 40 of the syringe 16 tightly interfaces with the interior walls of the pressure jacket 34. The syringe 16 and pressure jacket 34 are suitably connected via corresponding mating sections that facilitate connection of the syringe 16 to the injector 10.

The neck 44 of the discharge tip 46 contains an orifice 54 at its remote end, which communicates with an internal syringe cavity formed within the neck 44, the conical front wall 42, and the body 40 of the syringe 16. The rear end of the cavity 56 is further defined by a forward facing conical surface 58 of the syringe plunger 30. The conical surface 58 defines a slope that substantially conforms to the slope of the interior of the conical front wall 42 such that the conical surface 58 may engage the interior of the conical front wall 42 when the syringe plunger 30 is forwardly advanced and most or all of the liquid in the cavity 56 has been dispensed. The syringe plunger 30 is tightly slidable within the body 40 of the syringe 16 such that the cavity 56 has a variable volume.

Figure 3:
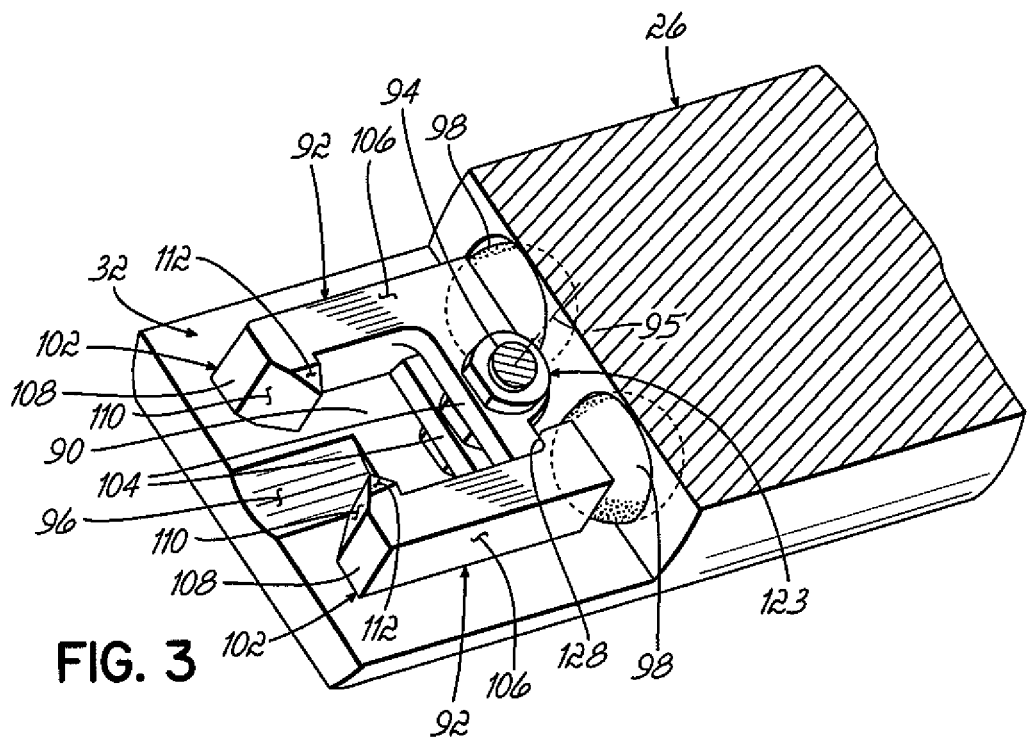
FIG. 3 is a sectioned perspective view of a gripper assembly of the drive ram shown in FIGS. 2A and 2B.
Figures 4, 5:
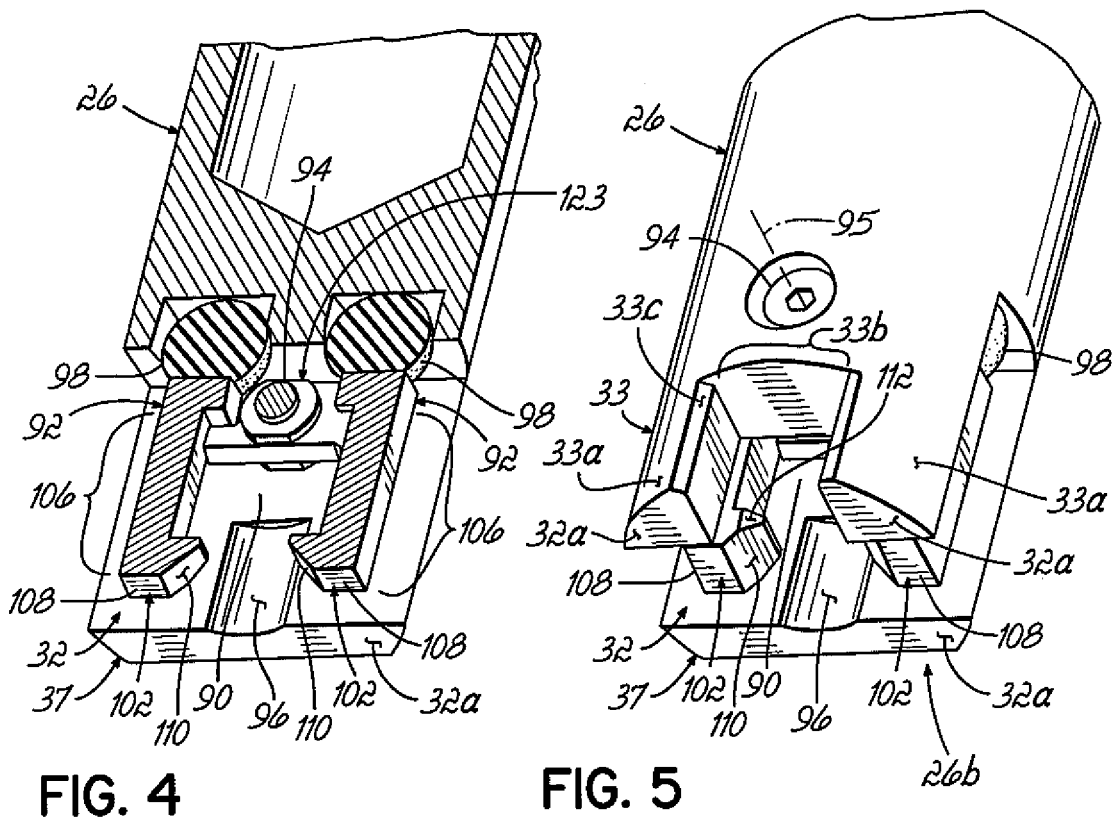
FIG. 4 is a further sectioned view of the gripper assembly of FIG. 3.
FIG. 5 is a perspective view of a drive ram of the injector of FIG. 1.
Figure 7:
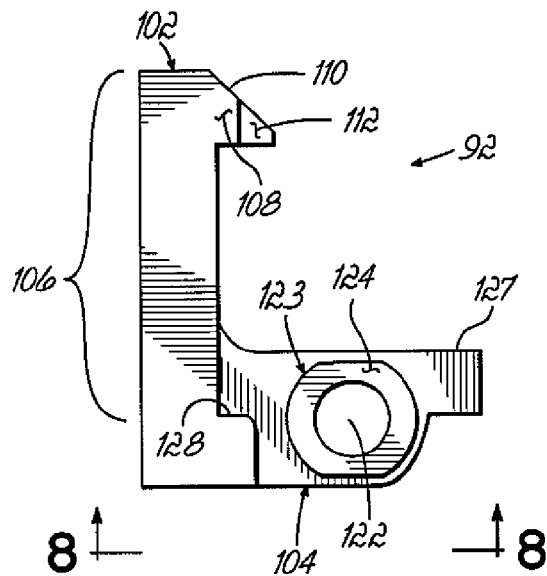
FIG. 7 is a top view of a gripper member of the gripper assembly of FIGS. 3-4.

With reference to FIGS. 2-5, the drive ram 26 is suitably interconnected with a diagrammatically represented motor 27 of the injector 10 such that the motor 27 can cause translational movement of the drive ram 26 generally along the longitudinal axis 24 of the drive ram 26. The drive ram 26 includes the gripper assembly 32, which engages the button 28 of the syringe plunger 30, such that translational movement of the drive ram 26 causes a corresponding motion of the syringe plunger 30. More specifically, and as shown in FIGS. 2 and 4, the button 28 of the syringe plunger 30 is located within a gripper cavity 90 of the gripper assembly 32 such that upon rearward motion of the drive ram 26 the gripper assembly 32 engages surfaces 109 of the button 28 to thereby cause corresponding rearward motion (i.e., withdrawal) of the syringe plunger 30 relative to the body 40 (e.g., such that fluid may be drawn into the cavity 56 of the syringe 16). Similarly, forward motion of the drive ram 26 generally along the longitudinal axis 24 causes forward faces 32a of the drive ram 26 to push a confronting surface 30a of the syringe plunger 30, such that fluid may be expelled from the cavity 56 of the syringe 16.

With reference to FIGS. 3-5, the gripper assembly 32 is disposed between two portions 33, 37 of the drive ram 26 (one of which is seen in FIGS. 3 and 4 and both of which are seen in FIG. 5 and, from a different angle, in FIGS. 2A and 2B), such that the button 28 of the syringe plunger 30 can be received therebetween. The first portion 33 includes two prongs 33a defining a gap 33b between them that is adapted to receive the button 28. The second portion 37 in this illustrative embodiment includes a depression 96 to further accommodate at least a portion of the button 28. The gripper assembly 32 includes two confronting gripper members 92 pivotally coupled about a pivot pin 94 disposed along a common pivot axis 95 that intersects axis 24 and is oriented substantially perpendicular to axis 24. The pivot pin 94 may be suitably coupled to a nut or similar fastener to cause engagement of the portions 33, 37 of the drive ram 26 or may, as shown in the exemplary embodiment of FIG. 5, be in the form of a screw or bolt extending between the portions 33, 37. The two gripper members 92 define a gripper cavity 90 therebetween, which is in registration (i.e. in a direction generally orthogonal to axis 24) with at least a portion of the gap 33b of the portion 33 of the drive ram 26. This registration facilitates receipt of the button 28 through gap 33b and into the cavity 90. Moreover, the gripper cavity 90 creates a locking engagement of the button 28, thereby restricting downward (i.e., toward bottom portion 37) and lateral (i.e., parallel to forward faces 32a) motion of the button 28.

As used herein, and for ease of understanding, the term "pivot" or the like refers to any type of movement, turning, flexing and/or elastic deformation of a structure or a portion thereof at least generally about a certain axis. Similarly, the term "pivotal interconnection" or the like refers to any type of interconnection that allows a structure to at least generally undergo a pivoting or pivotal-like motion when exposed to an appropriate force, including without limitation any interconnection that allows a structure or a portion thereof to move at least generally about a certain axis. Representative pivotal interconnections include the use of a flexing or elastic deformation of a structure or a portion thereof, as well as the use of relative motion between two or more structures that are typically in interfacing relation during at least a portion of the relative movement (e.g., a hinge connection; a ball and socket connection).

Moreover, use of directional terms herein, such as downward(ly), lateral(ly) and others are not intended to be limiting but may rather provide clarification based on orientations specific to depicted exemplary embodiments.

Figure 6:
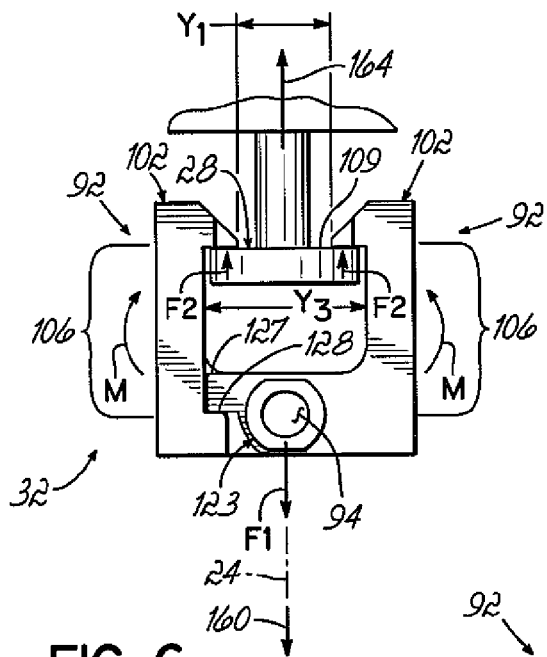
FIG. 6 is a top view of the gripper assembly of FIGS. 3-4 in a first position retaining a feature of a syringe plunger.
Figure 9:
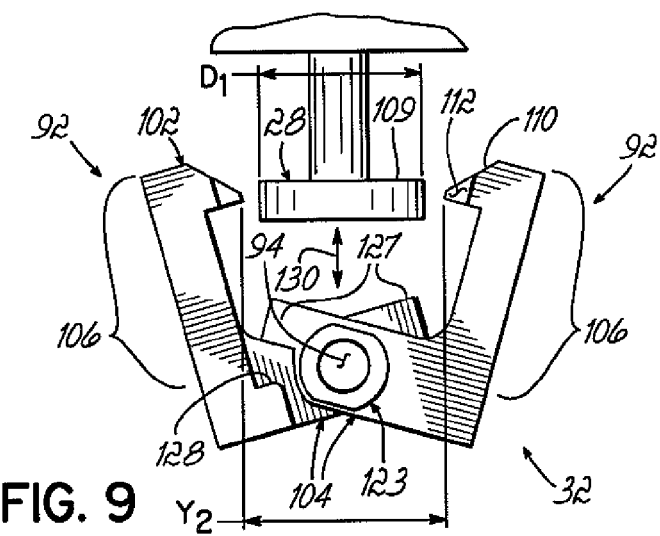
FIG. 9 is a top view of the gripper assembly of FIGS. 3-4 in a second position relative to the feature of FIG. 6.

With continued reference to FIGS. 3-5, and referring further to FIGS. 6 and 9, a plurality of biasing members 98, depicted here in the form of resilient balls or spheres, urge the gripper members 92 toward a first position, shown in FIGS. 3-5, in which first ends 102 of the gripper members 92 are spaced apart by a distance Y1 (FIG. 6), which is smaller than a diameter D1 (FIG. 9) of the button 28. This size relationship helps to keep button 28 interconnected with the gripper assembly 32 when the button 28 is located within the gripper cavity 90. While the biasing members 98 are depicted as resilient balls or spheres, persons of ordinary skill in the art will readily appreciate that the biasing members may take any other suitable forms including, without limitation, springs, piezoelectric materials or other devices. Similarly, while two biasing members are depicted, it is contemplated that the gripper assembly 32 may alternatively include biasing members in a number less than or in excess of two.

With particular reference to FIGS. 6-9, each of the gripper members 92 includes a first end 102, an opposing second end 104, and a main body portion 106 therebetween. Each of the first ends 102 includes an arm 108 extending in a direction toward the other gripper member 92. The first and second ends 102, 104, along with the main body portion 106 and arm 108, generally define the shape and dimensions of the gripper cavity 90 of the gripper assembly 32.

With reference to FIGS. 3-9, each arm 108 includes a front beveled surface 110 and an upper beveled surface 112 suitable to facilitate sliding motion of the button 28 into the gripper cavity 90. Furthermore, each prong 33a includes a top portion beveled surface 33c. These beveled surfaces facilitate engagement of the button 28 with the gripper members 92.

In one embodiment, illustrated in FIGS. 1 and 2, the syringe may be loaded from the rear of the pressure jacket, in which case the syringe 16 is loaded with the drive ram 26 retracted into housing 18 of the injector 10. The user disengages the face plate 22 from the injector housing 18 by translation of the faceplate in a direction perpendicular to the axis 24 of the drive ram to the position in FIG. 2B, and then moves the face plate away from the front surface of the injector to allow access to the internal aperture of the pressure jacket (aperture 26b). The user then installs a syringe 16 into aperture 26b, and returns the face plate to its original position shown in FIGS. 1 and 2A by moving the face plate against the front surface of the injector to the position shown in FIG. 2B, and translating the faceplate perpendicular to the axis 24 of the drive ram into its engaged position shown in FIGS. 1 and 2A.

In this exemplary type of loading, the translation of the faceplate perpendicular to axis 24 causes button 28 to be inserted into the cavity 90 of the gripper assembly 32. More specifically, the button 28 may slide between the two prongs 33a, such motion being facilitated by respective top portion beveled surfaces 33c on each prong 33a proximate the gap 33b. The button 28 may subsequently slide directly into cavity 90, coming to rest in the position shown in FIG. 6.

In an alternate situation, the drive ram may not be fully retracted, or the syringe may be loaded when the plunger is not at its rearwardmost position. In this circumstance, the button 28 may not be engaged to the gripper members 92 when the syringe is installed. Instead, the button 28 may be engaged axially between the top and bottom portions 33, 37 and between the gripper members 92. More specifically, forward motion of the ram 26 may cause the button 28 to be pushed against front beveled surfaces 110, thereby spreading the gripper members 92 apart from the first distance Y1 (FIG. 6) to the second, larger distance Y2 (FIG. 9) such that the button 28 can be received within the cavity 90.

In another case, in relative transverse motion of the button 28 and plunger drive ram 26, button 28 may potentially abut the upper beveled surfaces 112 of the gripper members 92, and slide downwardly into a position between the grippers 106 similar to that shown in FIG. 9. In this circumstance, sliding of the button 28 against the upper beveled surfaces 112 spreads the gripper members 92 apart from the first distance Y1 (FIG. 6) to a second, larger distance Y2 (FIG. 9) such that the button 28 can be received between the gripper members 106 as seen in FIG. 9. In the event the button 28 is loaded to a position between the grippers shown in FIG. 9, subsequent forward movement of the ram, as is required to advance the plunger for filling of the syringe, causes translation of the button relative into the cavity 90 in a direction parallel to axis 24, such that the gripper assembly 32 then secures the button 28 within cavity 90 as seen in FIG. 9.

Unloading of the syringe 16 from the injector, proceeds by transverse disengagement of the button from the gripper members 92, such as by disengaging the face plate 22 from the injector housing 18 with transverse motion to the position shown in FIG. 2B, or by other forms of disengagement as discussed above.

The drive ram 26 of the embodiment illustrated in detail herein, provides at least two methods of engaging the button 28. More particularly, the drive ram 26 can receive the button 28 axially, as well as in a direction that is traverse to the axis 16a of the syringe plunger 30, as explained above.

Other aspects of exemplary loading processes for the syringe 16 are described in a number of U.S. patents, such as those referenced herein. Persons of ordinary skill in the art will readily recognize that unloading of the syringe 16 may include sliding the button 28 in vertical or horizontal or any other directions away from cavity 90, not limited to those described above, and that a mechanism may be provided for positioning the gripper members 92 in the position shown in FIG. 9 to permit disengagement of the plunger button 28 without requiring transverse motion.

In one aspect of this embodiment, the spreading motion of the gripper members 92 is resisted by respective opposing forces exerted by the biasing member 98 against the second ends 104 of the gripper members 92. Once the button 28 is fully received within the cavity 90, the opposing forces exerted by the biasing members 98 cause the gripper members 92 to return to the first position where the first ends are spaced apart by the first distance Y1, thereby lockingly engaging the button 28 within the cavity 90.

With reference to FIGS. 6 and 9, the shape and dimensions of the gripper cavity 90 can be, but are not necessarily, chosen such that the button 28 of the syringe plunger 30 can tightly fit laterally therein (i.e., the width of the cavity or the dimension measured in a direction orthogonal to the axis 24). In other words, the gripper cavity 90 may be such that the diameter D1 (FIG. 9) of the button 28 may be substantially equal to the distance Y3 (FIG. 6) between the main body portions 106 of the gripper members 92. Moreover, the shape and dimensions of the gripper cavity 90 can be, but are not necessarily, chosen such that the button 28 fits loosely therein in a direction along the axis 24 (i.e., the length of the cavity 90). Tight lateral fitting facilitates positive engagement of the button 28 by the gripper members 92 with surfaces 109 (FIG. 6) of the button 28. By contrast, loose fitting of the button 28 along a direction of the axis 24 may reduce the likelihood of temporary or permanent bonding of the button 28 with surrounding surfaces of the cavity 90, especially if and when medical fluid (e.g., contrast media) leaks into the cavity 90. In the exemplary embodiment shown, the length of the cavity 90 is depicted being larger than the width thereof, to accommodate the dimensions of the exemplary button 28. Persons of ordinary skill in the art will, however, readily appreciate that this dimensional relationship between the width and length of the cavity 90 is only illustrative and actual geometry may differ from that shown and described herein.

Figure 8:
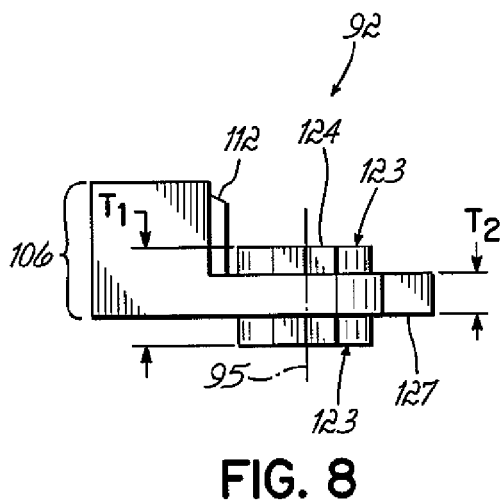
FIG. 8 is an end view of the gripper member of FIG. 7 taken along line 8-8 of FIG. 7.

With reference to FIGS. 3-8, the second end 104 of each gripper member 92 has an aperture 122 defined therein that is configured to receive the pivot pin 94 therethrough. A contact portion 123 of the second end 104 of each gripper member 92 surrounds the common pivot axis 95 of the pivot pin 94 and is shown as exhibiting a thickness T1 that is greater than a thickness T2 of adjacent portions of the second end 104 (FIG. 8). In the exemplary embodiment of FIGS. 3-8, the contact portion 123 takes the form of a hub surrounding the aperture 122, although it is contemplated that the contact portion 123 may exhibit any other appropriate shape.

Figure 6A:
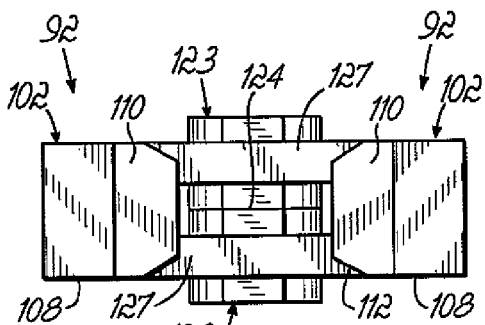
FIG. 6A is an end view of the gripper assembly as shown in FIG. 6, from the plunger side.

As best observed in FIGS. 3 and 8, the thickness T1 of the contact portion 123 permits sliding pivotal motion of the gripper members 92 with respect to one another. Direct contact between the gripper members 92 during this sliding pivotal motion is thus limited to the confronting surfaces 124 of the respective contact portions 123. The remaining surfaces of the second ends 104 of each gripper member 92 are spaced from the corresponding surfaces on the other gripper member 92, as seen in FIG. 6A. This space minimizes the resistance to movement of the gripper members 92 that might otherwise be caused by medical fluid (contrast media) that the gripper members 92 might inadvertently be exposed to. An advantage of limiting contact to the confronting surfaces 124 lies in a resulting minimization of surfaces exposed to contrast media and/or other fluid that may leak into the cavity 90 and that may otherwise interrupt a smooth sliding motion of the gripper members 92 with respect to one another. Moreover, because the confronting surfaces 124 are adjacent the aperture 122 (the pivot axis of the gripper members 92), any resistance to pivotal movement of the gripper members 92 that might be caused by contrast media in this area will be minimized.

With continued reference to FIGS. 3-8, the second end 104 of each gripper member 92 includes a finger 127 configured to extend outwardly. In the exemplary assembled condition of FIG. 6, each finger 127 further extends toward the axis 24 of the drive ram 26 and toward the other gripper member 92. In addition, the second end 104 of each gripper member 92 includes a ledge 128 that is configured to interface with the corresponding finger 127 on the opposite gripper member 92. This interface of each finger 127 with the corresponding ledge 128 is such that the gripper members 92 are restricted from pivotally moving toward one another beyond the positions depicted in FIGS. 3-5. In some embodiments, the relationship between the fingers 127 and respective ledges 128 of the gripper assembly 32 may be such that the gripper members 92 pivot in substantial unison. For example, in such embodiments, if one gripper member 92 is pivoted such that the first end 102 thereof is resultantly spaced from the axis 24 by a distance, the design of the gripper assembly 32 would be such that the other gripper member 92 would be simultaneously pivoted such that the first end 102 thereof is resultantly spaced from the axis 24 by substantially the same distance.

With reference to FIG. 9, the gripper members 92 are depicted in the second position, with the first ends 102 being spaced apart a distance Y2 greater than the distance Y1 at the first position described above. This second position may be said to facilitate insertion and removal of the button 28 respectively into and from the gripper cavity 90, as indicated by arrow 130. As explained above, the front beveled surfaces 110 and upper beveled surfaces 112 on each gripper member 92 may be utilized to facilitate insertion of the button 28 into the cavity 90. Moreover, because the gripper members 92 are seated on one another with their respective contact portions 123, fingers 127, and ledges 128 in engagement as described above, the gripper members 92 are able to pivot together, or float, to facilitate receiving the button 28 of the drive ram 26 therebetween. This may be particularly helpful in locating the button 28 between the gripper members 92 when the button 28 is offset from the drive ram 26.

As stated above, and referring to FIGS. 6 and 9, the gripper assembly 32 includes gripper members 92 that are pivotable about a common pivot pin 94 that intersects the axis 24 of the drive ram 26 and that is oriented substantially perpendicular to that axis 24. Rearward movement of the drive ram 26 in a direction depicted by arrow 160 (FIG. 6) exerts a first force F1 at a point defined by the pivot pin 94. Force F1 is transferred by the gripper members 92 against points of engagement on surfaces 109 of the button 28. This first force F1 induces second, oppositely directed reaction (e.g., normal) forces F2 applied by the plunger 30 on the gripper members 92. The second forces F2 are generally in the direction indicated by arrow 164 (FIG. 6) which is generally parallel to or further coaxial with the axis 24 (FIG. 2) of the drive ram 26. Each gripper member therefore is acted on by forces F1, applied at contact portion 123, and F2, applied at arm 108.

As a result of the gripper member geometry discussed above, forces acting on the gripper assembly 32 during rearward movement of the drive ram 26 do not generate moments or torques that would cause pivoting of the gripper members 92 in directions outwardly from button 28, thereby reducing the likelihood of disengagement of the gripper members 92 from the button 28. Rather, in some embodiments, forces F1, F2 acting on gripper members 92 during rearward movement of drive ram 26 urge the gripper members 92 toward one another, thereby facilitating secure engagement of the button 28 by the gripper assembly 32. In other words, the resultant of forces applied to each gripper member 92 is a moment or torque M that tends to pivotally urge the gripper members 92 in directions toward button 28, as depicted in FIG. 6.

While the above has been described with reference to a medical fluid injector having a single syringe, persons of ordinary skill in the art will appreciate that the same principles are similarly applicable to injectors having syringes in a number in excess of one. For example, and without limitation, the above-described embodiments are applicable to dual-head injectors as well as rear-, side-, and front-loadable injectors (e.g., Optivantage™ DH injector, Angiomat™ Illumena™ injector).

When introducing elements of the present invention (E.G., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

As various changes could be made in the above-described aspects and exemplary embodiments without departing from the scope of the invention, it is intended that all matter contained in the above description shall be interpreted as illustrative and not in a limiting sense.

What is claimed is:

1. A drive ram for a medical fluid injector, the drive ram comprising:
   a first gripper member pivotally interconnected with a plunger engaging end of the drive ram, wherein the first gripper member comprises a first end, a second end, and a main body portion between the first and second ends of the first gripper member, wherein the first end of the first gripper member is engageable with a syringe plunger, and wherein the second end of the first gripper member comprises a first aperture and a first raised contact portion;
   a second gripper member pivotally interconnected with the plunger engaging end of the drive ram, wherein the second gripper member comprises a first end, a second end, and a main body portion between the first and second ends of the second gripper member, wherein the first end of the second gripper member is engageable with a syringe plunger, and wherein the second end of the second gripper member comprises a second aperture and a second raised contact portion; and
   a pivot pin within the first aperture of the first gripper member and the second aperture of the second gripper member;
   wherein contact between the first and second gripper members is limited to the respective first and second raised contact portions;
   wherein each of the first and second gripper members is pivotable about a common pivot axis that coincides with the pivot pin; and
   wherein the first and second gripper members are pivotable between a first position and a second position, the first ends of the first and second gripper members being spaced apart by a first distance when the first and second gripper members are in the first position, and the first ends being spaced apart by a second distance greater than the first distance when the first and second gripper members are in the second position.

2. The drive ram of claim 1, wherein the first and second gripper members are configured to move in substantial unison between the first and second positions.

3. The drive ram of claim 1, wherein each of the first and second gripper members further comprises an arm, the arm extending from the first end in a direction toward the longitudinal reference axis.

4. The drive ram of claim 1, wherein the drive ram extends along a central, longitudinal reference axis, the drive ram further comprising a cavity substantially defined between the first and second gripper members, the cavity having a length measured along the reference axis that is greater than a width measured perpendicular to the reference axis.

5. The injector of claim 1, wherein the first raised contact portion of the first gripper member comprises a first hub that is disposed about the first aperture, and wherein the second raised contact portion of the second gripper member comprises a second hub that is disposed about the second aperture.

6. The injector of claim 1, wherein a thickness of the first raised contact portion of the first gripper member is greater than a thickness of a first adjacent portion to the first raised contact portion of the second end of the first gripper member, and wherein a thickness of the second raised contact portion of the second gripper member is greater than a thickness of a second adjacent portion to the second raised contact portion of the second end of the second gripper member.

7. The injector of claim 1, the second end of each of the first and second gripper members comprises a finger, wherein the second end of each of the first and second gripper members comprises a ledge, and wherein engagement of the finger of the first gripper member with the ledge of the second gripper member and engagement of the finger of the second gripper member with the ledge of the first gripper member limits further movement of the first ends of the first and second gripper members toward one another.

8. A medical fluid injector comprising the drive ram of claim 1.

9. The injector of claim 8, further comprising:
   a syringe mounted to the injector.

10. The injector of claim 9, wherein the syringe has medical fluid disposed therein.

11. The injector of claim 9, wherein the syringe has contrast media disposed therein.

12. The injector of claim 9, wherein the syringe comprises a plunger, and wherein at least a portion of the plunger is located between the first and second gripper members of the drive ram.

\* \* \* \* \*